(12) United States Patent
Bouchier et al.

(10) Patent No.: US 6,468,462 B1
(45) Date of Patent: Oct. 22, 2002

(54) METHOD FOR MAKING AN ELECTRODE BALLOON

(75) Inventors: Mark S. Bouchier, Lakeville, MN (US); Randy L. Morningstar, Brooklyn Park, MN (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 09/565,995

(22) Filed: May 6, 2000

Related U.S. Application Data

(62) Division of application No. 09/026,349, filed on Feb. 19, 1998, now Pat. No. 6,091,993.

(51) Int. Cl.⁷ .............................. B29C 45/44; A61F 7/00
(52) U.S. Cl. ............ 264/318; 264/328.1; 428/DIG. 58; 607/98
(58) Field of Search .............................. 264/318, 328.1, 264/219, 334; 425/DIG. 58; 29/450, 454, 448, 451; 607/98; 606/41, 32

(56) References Cited

U.S. PATENT DOCUMENTS

| | | | | |
|---|---|---|---|---|
| 2,583,441 A | * | 1/1952 | Palmer | 164/347 |
| 3,104,425 A | * | 9/1963 | Crane et al. | 249/142 |
| 4,342,442 A | * | 8/1982 | Perkins et al. | 249/64 |
| 4,383,673 A | * | 5/1983 | Laprade et al. | 249/142 |
| 4,447,373 A | * | 5/1984 | Chappell et al. | 156/146 |
| 4,559,951 A | | 12/1985 | Dahl et al. | |
| 4,735,208 A | * | 4/1988 | Wyler et al. | 600/377 |
| 4,819,647 A | * | 4/1989 | Byers et al. | 128/903 |
| 4,955,377 A | | 9/1990 | Lennox et al. | |
| 5,037,497 A | | 8/1991 | Stypulkowski | |
| 5,076,096 A | | 12/1991 | Blyler, Jr. et al. | |
| 5,084,044 A | | 1/1992 | Quint | |
| 5,105,808 A | | 4/1992 | Neuwirth et al. | |
| 5,151,100 A | | 9/1992 | Abele et al. | |
| 5,191,883 A | | 3/1993 | Lennox et al. | |
| 5,223,205 A | | 6/1993 | Jackowski et al. | |
| 5,277,201 A | | 1/1994 | Stern | |
| 5,368,591 A | | 11/1994 | Lennox et al. | |
| 5,374,261 A | | 12/1994 | Yoon | |
| 5,407,627 A | | 4/1995 | Schiller et al. | |
| 5,443,470 A | | 8/1995 | Stern et al. | |
| 5,496,311 A | | 3/1996 | Abele et al. | |
| 5,498,388 A | * | 3/1996 | Kodai et al. | 264/263 |
| 5,562,720 A | * | 10/1996 | Stern et al. | 606/32 |
| 5,693,080 A | | 12/1997 | Wallsten et al. | |
| 5,713,942 A | | 2/1998 | Stern et al. | |
| 5,769,846 A | | 6/1998 | Edwards et al. | |
| 5,769,880 A | | 6/1998 | Truckai et al. | |
| 5,779,698 A | | 7/1998 | Clayman et al. | |
| 5,783,126 A | * | 7/1998 | Anderson et al. | 264/102 |
| 5,848,969 A | | 12/1998 | Panescu et al. | |
| 5,957,962 A | | 9/1999 | Wallsten et al. | |
| 6,091,993 A | | 7/2000 | Bouchier et al. | |

\* cited by examiner

*Primary Examiner*—Jill L. Heitbrink
(74) *Attorney, Agent, or Firm*—Jeffrey J. Hohenshell

(57) ABSTRACT

A method for making an electrode balloon is disclosed. The method includes the steps of filling a mold cavity with a polymer and heating the polymer to a temperature to cure the polymer. The balloon is particularly suitable for use in a surgical procedure for ablating tissue in the uterus.

8 Claims, 3 Drawing Sheets

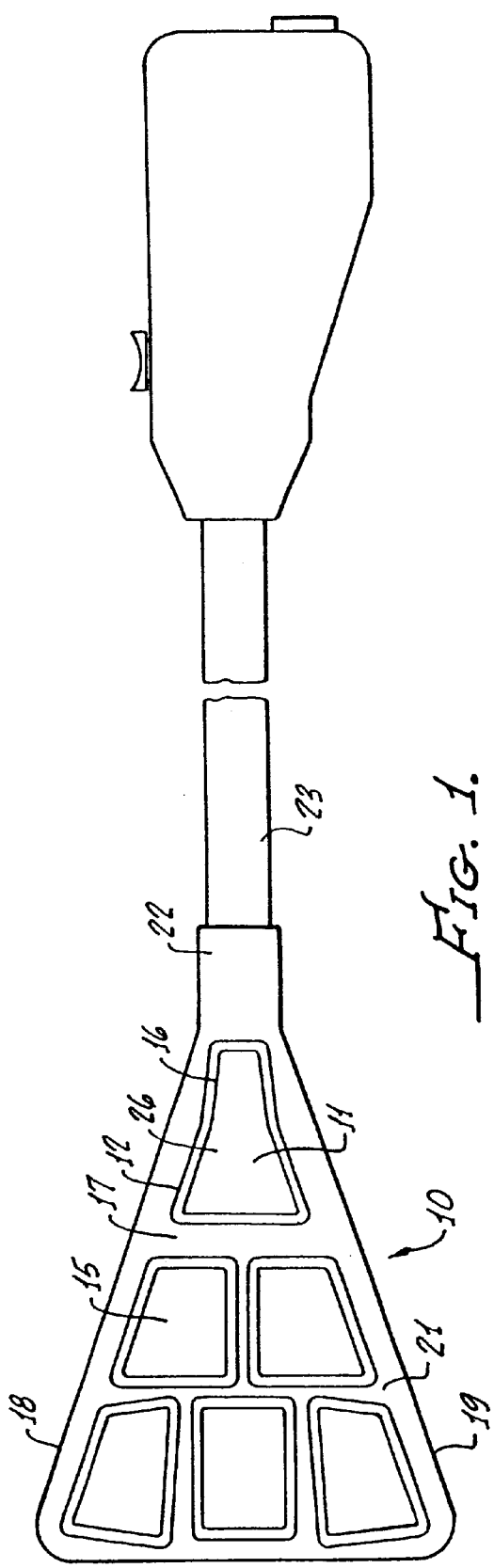
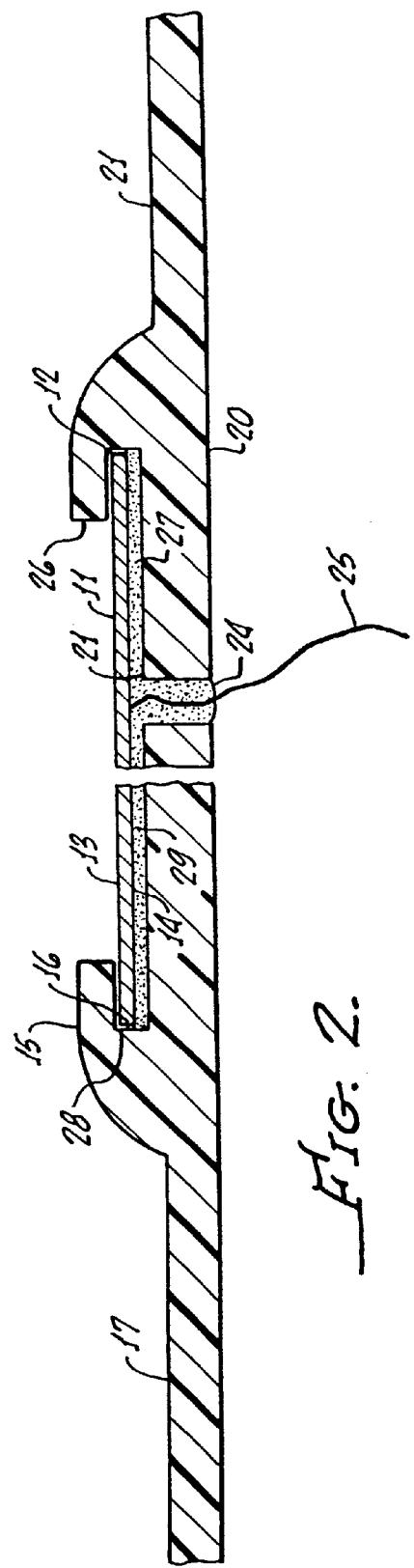

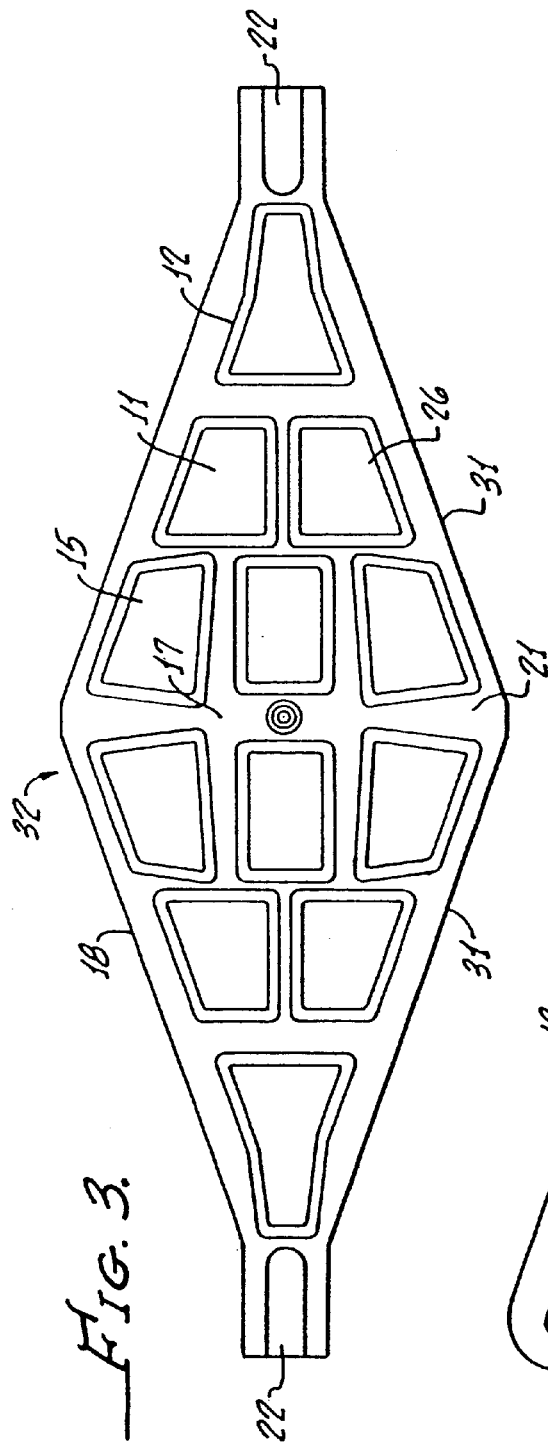
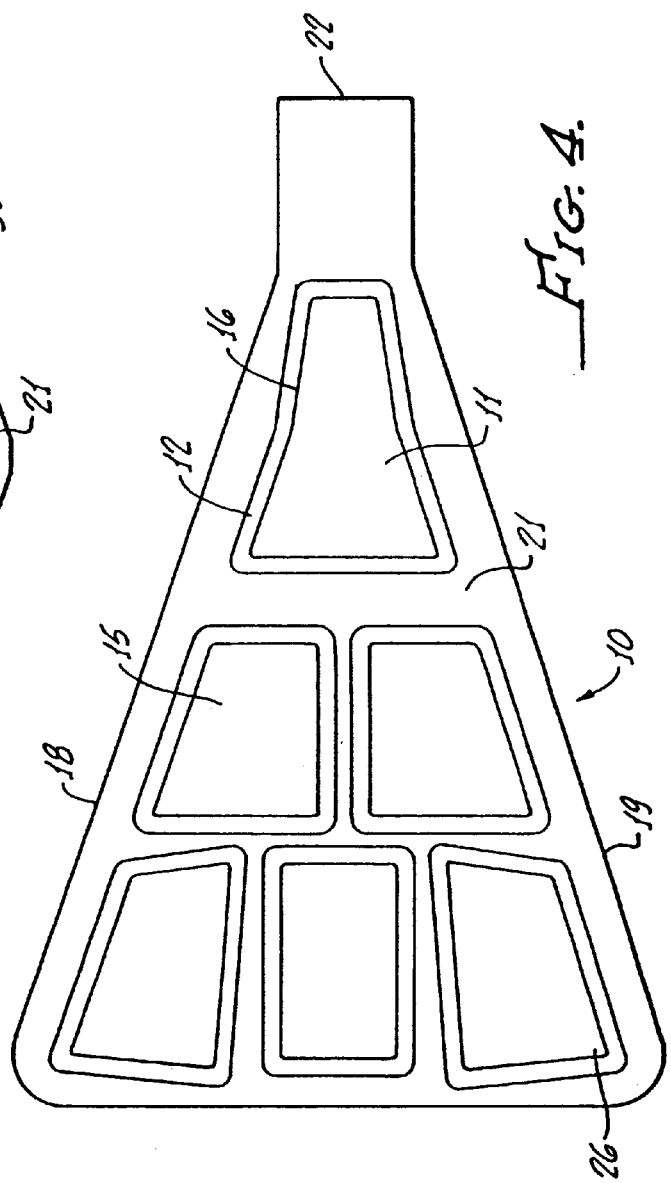

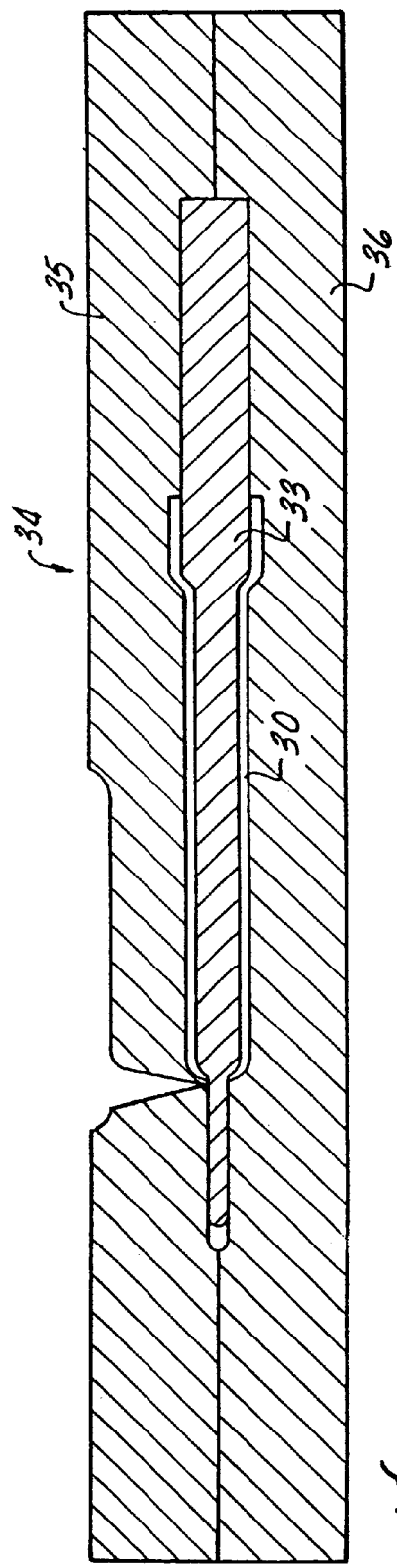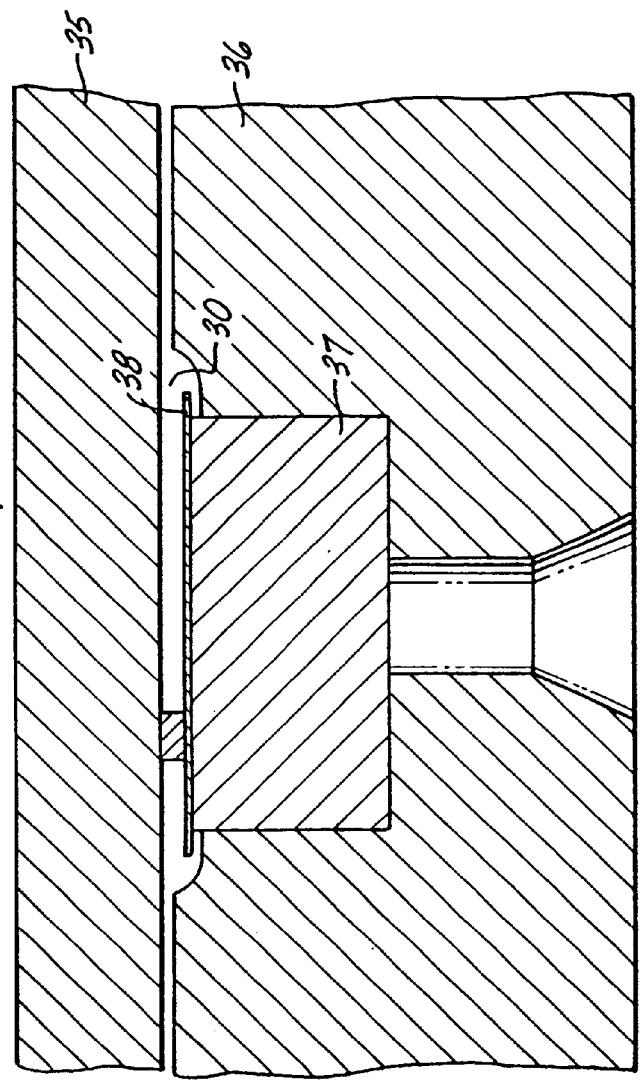
Fig. 5.
Fig. 6.

METHOD FOR MAKING AN ELECTRODE BALLOON

CROSS-REFERENCE TO RELATED APPLICATIONS

This application is a divisional of U.S. patent application Ser. No. 09/026,349, filed Feb. 19, 1998 now U.S. Pat. No. 6,091,993.

FIELD OF THE INVENTION

This relates to a flexible support for a thin electrically conductive electrosurgical electrode. More particularly, a circumferential frame shaped to capture an edge of the electrosurgical electrode.

BACKGROUND OF THE DISCLOSURE

U.S. Pat. No. 5,277,201 has a balloon with electrodes to delivery radio frequency energy attached to the balloon for treatment of the endometrium.

U.S. Pat. No. 5,443,470 has a regulated heating device with a balloon having electrodes for delivery of radio frequency energy to the endometrium.

U.S. Pat. No. 5,562,720 has a method of making a balloon with electrodes attached thereto including use of sheet or curing a coating on a mandrel to form the balloon to carry electrodes or sensors.

The method of manufacture for the expandable balloon includes casting silicone elastomer dispersion over the radio frequency electrodes and-allowing the dispersion to remain volatile for an extended period of time before curing and completing the balloon assembly. The casting process embeds the electrodes in a consistent wall thickness of elastomer. The electrosurgical electrodes are not well captured by the balloon during inflation of the electrode containing balloon within the uterus. The casting process also produces a minimum wall thickness of the elastomer which may be too thick and makes the balloon bulky when it is folded down and placed into the delivery sheath of the device. As a result, product yields have been low due to electrode dislocation on the balloon surface during fold down into the sheath. Average production throughput times are estimated in days to complete the balloon casting and assembly.

U.S. Pat. No. 4,955,377 has a balloon with an electrode there inside which heats therethrough.

SUMMARY OF THE INVENTION

A flexible support for a thin electrically conductive electrosurgical electrode includes an edge therearound defining its shape about its major surfaces. One or more circumferential frames each shaped to capture the edge of the electrosurgical electrode are preferably on the support. An under cut is most preferably on the circumferential frame for substantially holding and enclosing the edge of the electrosurgical electrode. A membrane may be integral with the one or more circumferential frames. The membrane can extend from each circumferential frame and might be coextensive with each circumferential frame. It is preferred that the membrane has a thinness sufficient to allow expansion in deference to the one or more circumferential frames. The one or more circumferential frames, the under cut and the membrane made in the preferred embodiment of the flexible support be made from a flexible polymer.

The flexible polymer of the preferred embodiment has a percent of elongation in the range of 500% to 1500%. The one or more circumferential frames and the integral membrane form most preferably an inflatable balloon with an interior surface and an exterior surface with an inflation port therethrough. The under cut on the one or more circumferential frames may be situated, placed or disposed for substantially holding and enclosing the edge of each electrosurgical electrode on the exterior surface of the balloon. The membrane may expand upon ainflation of the inflatable balloon. The one or more circumferential frames can include a window opening to a recess peripherally surrounded by the under cut and a wall within the under cut is disposed to most preferably abut the edge of electrosurgical electrode, the window opening shaped as the major surface of the electrosurgical electrode while sized slightly smaller to define the under cut. The flexible polymer is in the preferred embodiment an elastomeric material having a high dielectric. The flexible polymer is most preferably a silicone with a temperature resistance of at least 100 degrees centigrade. An adhesive can be if desired applied to bond one major surface of the electrosurgical electrode within the circumferential frame.

The membrane is desired to be integral with the one or more circumferential frames, the membrane resides within the circumferential frame and forms the exterior surface of a balloon.

A method of making a flexible support for a thin electrically conductive electrosurgical electrode may have steps. Providing a mold cavity to receive and shape the flexible support is a preferred step. The mold most preferably has an unpolished surface finish to enhance release properties during removal of the flexible support. A step could include filling the mold cavity with a thermosetting polymer. The step of heating the mold cavity to a temperature sufficient to cure the thermosetting polymer into one or more circumferential frames each shaped to capture the edge of the electrosurgical electrode might follow. An under cut on the circumferential frame most preferably is for substantially holding and enclosing the edge of the electrosurgical electrode. A membrane is desired to be integral with the one or more circumferential frames for extending from each circumferential frame and coextensive with each circumferential frame. The membrane. may have a thinness sufficient to allow expansion in deference to the one or more circumferential frames. The one or more circumferential frames, the under cut and the membrane could in a step of the preferred method be made from the thermosetting polymer. The steps of folding the flexible support and sealing the abutting sides thereof to form a balloon can be performed if the molding is of a flat preform. The step of inserting a core into the mold cavity to form a balloon during the step of filling may be an alternate step.

A mold for making a flexible support balloon for a thin electrically conductive electrosurgical electrode with an edge therearound defining its shape about its major surface is preferred. Top and bottom platens may be movably supported to fit together for the preferred mold. The top and bottom platens can therein define a mold cavity when they are fit together. A mold cavity is preferably disposed in either the top platen or bottom platen. A pedestal is located preferably upstanding within the mold cavity. It is desired that a plate in the preferred mold be mounted atop the pedestal.

The flexible support is part of an ablation device for delivering necrosis to the endometrium to eliminate uterine bleeding. The flexible support is preferably in the shape of an expandable balloon carrying electrosurgical electrodes to deliver radio frequency energy to the endometrial tissue thereby causing necrosis to the endometrium.

To overcome the difficulties of previous methods and designs, an apparatus design and method of manufacture and equipment therefor have been created to address the issues with existing balloons. The new design consists of a method for molding the balloon with specific molded locations -for the electrosurgical electrodes. These molded locations include an under cut to capture the edge of the electrosurgical electrode. The molded balloon includes a membrane between the electrode locations. The membrane preferably has a thinner wall section. This difference in wall section allows the balloon to expand within the uterus more uniformly without dislocating the electrosurgical electrodes from the balloon surface. Thus the uterine space is filled more uniformly for distributing the electrosurgical electrodes and subsequently radio frequency energy to more uniformly within the uterine space. This design and method of manufacture also eliminates the inconsistencies of the casting method by molding a uniform, consistent geometry with varying yet controlled wall thickness. The molding process also allows for a thinner balloon wall thickness which is desirable for fold down of the balloon into the device sheath without electrode dislocation form the balloon surface. This thinner wall section allows for a smaller device sheath diameter which is also desirable for insertion and deployment of the balloon into the uterus.

BRIEF DESCRIPTION OF THE DRAWINGS

FIG. 1 is a perspective view of the electrosurgical electrode balloon shown inflated as in the procedural mode.

FIG. 2 is a partial enlarged side view in cross section taken along line 2—2 as shown in FIG. 1 with particular emphasis on the relationship of the electrosurgical electrode and the balloon in the area of one circumferential frame.

FIG. 3 is an enlarged front view of the balloon as molded in a flat form with electrosurgical electrodes installed but before heat sealing the edges to form a complete balloon as shown in FIG. 1.

FIG. 4 is a partial enlarged side view in cross section taken along line 2—2 as shown in FIG. 1 with particular emphasis on the relationship of the electrosurgical electrode and the balloon in the area of one circumferential frame.

FIG. 5 is a schematic representation of the mold and its core shown as a side view in cross section to illustrate the way in which a balloon is formed by molding.

FIG. 6 is an enlarged partial detail of the mold cavity used to form one under cut, window opening, circumferential frame and the membrane thereabout.

DETAILED DESCRIPTION OF THE DRAWINGS

Uterine balloon therapy to treat dysfunctional uterine bleeding with radio frequency electrodes is described in the patents referenced in the background of this disclosure. To overcome the difficulties of previous manufacturing and balloon designs, an apparatus and method of making and equipment therefor have been created to improve existing balloons. The disclosed balloon and method for molding has specific molded locations to receive electrosurgical electrodes. These molded locations capture each electrode to the exterior of the balloon. Between the molded locations containing the electrodes the balloon has a flexible wall section allowing expansion within the uterus without dislocating the electrosurgical electrodes from the balloon. Thus the uterus is filled uniformly for distributing the electrosurgical electrodes and applying radio frequency energy to the uterine walls.

Inconsistencies of casting or sheet fabrication described in the patents identified are eliminated by molding a consistent geometry balloon with varying yet controlled wall thickness. The molding process also allows for a thinner balloon wall thickness that is desirable for folding the balloon, placement of the balloon in a sheath and delivery and inflation of the balloon in the uterus. The molded locations permit the described use of a sheath without electrode dislocation from the balloon. This thinner wall sections allow a smaller package with a minimum sheath diameter desirable for insertion and deployment of the balloon into the uterus.

A flexible support 10 is shown in the figures and disclosed herein for carrying a thin electrically conductive electrosurgical electrode 11. The preferred electrosurgical electrode 11 is a polymeric film made conductive by metalization. The conductive film of choice is a substrate of Mylar polymer on to which copper is electro-deposited as a film. That film and the polymer are about 0.0254 mm thick, see FIG. 2. Each electrosurgical electrode 11 includes an edge 12 therearound defining its shape about its major surfaces 13 and 14. From the figures it can be seen and understood that various shapes of electrosurgical electrodes 11 may be used. The particular shape desired is a function of the organ and its tissue to be treated by ablation.

One or more circumferential frames 15 form the molded locations for electrosurgical electrode 11 support and containment. Each circumferential frame 15 is shaped to capture the edge 12 of one of the electrosurgical electrodes 11 on the support 10. An under cut 16, best seen in FIG. 2, provided beneath each circumferential frame 15 locates each respective electrosurgical electrode 11 for substantially holding and enclosing the edge 12 of the electrosurgical electrode 11. A membrane 17 integral with the one or more circumferential frames 15 extends there beneath and therebetween to form a balloon wall 18 that is about 0.254 mm thick. The membrane 17 thus extends from each circumferential frame 15 and is coextensive with each circumferential frame 15 forming a continuous inflatable bladder 19, as shown in FIGS. 1 and 4. The membrane 17 has a thinness sufficient to allow expansion of the membrane 17 in deference to each of the one or more circumferential frames 15. The one or more circumferential frames 15, the under cut 16 and the membrane 17 are molded into an integral flexible support 10.

A flexible polymer selected for its ability to retain inflation gas, liquid and/or fluid and accommodate the heat of ablation is used to mold the flexible support 10. The flexible polymer of the preferred embodiment has a percent of elongation in the range of 500% to 1500%. The flexible polymer is an elastomeric material having a high dielectric. The flexible polymer is most preferably a silicone with a temperature resistance of at least 100 degrees centigrade. The silicone preferred is supplied by Applied Silicone Corporation, of Ventura, Calif. as their LSR-30 part number 40025 with physical characteristics including 600% elongation per ASTM D412, durometer 30 Shore A, tensile strength 950 psi, tear strength 150 ppi and linear shrinkage during cure 2%. That initially liquid silicone rubber is medical grade for the support and it performs acceptable in tests of burst strength, dielectric strength (30,000 megohms), temperature resistance and biocompatibility. The flexible support 10 and its one or more circumferential frames 15 and the integral membrane 17 form an inflatable balloon 19 including an interior surface 20, in FIG. 2, and an exterior surface 21, in FIGS. 1, 2, 3 and 4, with an inflation port 22 therethrough. The inflation port 22 is circular in cross section to cooperate with a delivery sheath 23 as described in the patents in the background and as understood by skilled artisans and medical practitioners.

Each under cut 16 on each of the one or more circumferential frames 15 situated, placed or disposed for substantially holding and enclosing the edge 12 each electrosurgical electrode 11 that the major surface 14 of the electrosurgical electrode 11 rest against the exterior surface 21 of the inflatable balloon 19.

The membrane 17 is integral with the one or more circumferential frames 15, the membrane 17 resides within the circumferential frame 15 and forms the exterior surface 21 of balloon 19. The membrane 17 is thin so as to expand upon inflation of the inflatable balloon 19 before and/or to a greater extent than each of the one or more circumferential frames 15. The membrane 17 is continuous except at the port 22 and at each of the one or more circumferential frames 15 there can be a hole 24 to pass a conductor 25 to couple the electrosurgical electrode 11 held therewithin to a source of electrosurgical energy (not shown) during use in ablating the inside of the uterus. The electrosurgical electrodes 11 when made of electrically conductive polymeric film should have less extensibility than the membrane 17 of the inflatable balloon 19. Thus each of the one or more circumferential frames 15 resist change in shape during inflation of the inflatable balloon 19. The extensibility of each of the one or more circumferential frames 15 is desirably about that of the conductive film edge 12 of the electrosurgical electrodes 11. Consequently, each of the one or more circumferential frames 15 reinforces the inflatable balloon 19 so that expansion during inflation is primarily in the membrane 17 between the one or more circumferential frames 15 and not in the portions of the membrane 17 within each of the one or more circumferential frames 15.

Each of the one or more circumferential frames 15 includes a window opening 26 to a recess 27 peripherally surrounded by the under cut 16 and a wall 28 within the under cut 16 is disposed to most preferably abut the edge 12 of electrosurgical electrode 11, all of this is best shown in the enlarged side view in cross section in FIG. 2. The window opening 26 has shape of major surfaces 13 and 14 of the electrosurgical electrode 11 and as is apparent from FIGS. 1, 3 and 4 various electrosurgical electrode 11 shapes are desired to treat with ablation the inside of the uterus. The recess 27 and its respective electrosurgical electrode 11 are sized similarly and the window opening 26 therefor is sized slightly smaller to define the under cut 16 and retain the inserted electrosurgical electrode 11. An adhesive 29 can be applied to bond major surface 14 of the electrosurgical electrode 11 within the circumferential frame 15 and to seal the hole 24 for the conductor 25, see FIG. 2.

A method of making flexible support 10 for thin electrically conductive electrosurgical electrode 11 has steps. Providing a mold cavity 30 to receive and shape the flexible polymer of the flexible support 10 is a step. The mold cavity 30 has an unpolished surface finish (not shown) to enhance release properties during removal of the flexible support 10 molded or formed therein. A step could include filling the mold cavity 30 with a thermosetting polymer such as silicone. The step of heating the mold cavity 30 to a temperature sufficient to cure the thermosetting polymer into the membrane 17 with one or more circumferential frames 15 each shaped to capture the edge 12 of the electrosurgical electrode 11 might follow. The mold cavity 30 has under cut 16 within the circumferential frame 15 for substantially holding and enclosing the edge 12 of electrosurgical electrode 11 so that under cut 16 is in a step formed during filling and curing. The preferred liquid silicone rubber is at room temperature before injection or transfer into the mold cavity 30 at 1000 psi. During curing the mold cavity 30 is heated to a range of 110 to 160 degrees centigrade depending of mold mass and ambient temperature. The cure time in the mold cavity 30 at 110 to 160 degrees centigrade is about 2 to 5 minutes. Membrane 17 is desired to be integral with the one or more circumferential frames 15 for extending from each circumferential frame 15 and for being coextensive with each circumferential frame 15. The membrane 17 is molded in the mold cavity 30 with a thinness sufficient to allow expansion in deference to the one or more circumferential frames 15. The one or more circumferential frames 15, the under cut 16 and the membrane 17 could in a step of the method be molded into inflatable silicon balloon 19. The steps of folding the flexible support 10 and sealing abutting sides 31 in FIG. 3 in an alternate configuration thereof to form inflatable balloon 19 can be performed if the mold cavity 30 is of a flat preform 32. The step of inserting a core 33 into the mold cavity 30 to form balloon 19 during the step of filling may be an alternate step, as depicted in FIG. 5.

A mold 34 for making flexible support balloon 19 for thin electrically conductive electrosurgical electrode 11 with edge 12 therearound defining its shape about its major surfaces 13 and 14 is shown in FIG. 6. Top and bottom platens 35 and 36 may be movably supported to fit together for the mold 34 to define the mold cavity 30. The top and bottom platens 35 and 36 therein may establish the mold cavity 30 of the preform shown in FIG. 3 or FIG. 4 as only a part thereof is illustrated. The mold cavity 30 may be disposed in either the top platen 35 or bottom platen 36. A pedestal 37 is located preferably upstanding within the mold cavity 30. It is desired that a plate 38 in the mold cavity 30 be mounted atop the pedestal 37.

The preferred embodiment of thin flexible support 10 is part of an ablation device for delivering necrosis to the endometrium to eliminate uterine bleeding. The flexible support 10 is preferably in the shape of expandable balloon 19 carrying electrosurgical electrodes 11 to deliver radio frequency energy to the endometrial tissue thereby causing necrosis to the endometnum.

While a particular preferred embodiments have been illustrated and described the scope of protection sought is in the claims that follow.

What is claimed is:

1. A method of making a flexible support for a thin electrically conductive electrosurgical electrode comprising the following steps:

providing a mold cavity to receive and shape the flexible support, the mold cavity having an unpolished surface finish;

filling the mold cavity with a thermosetting polymer; heating the mold cavity to a temperature sufficient to cure the thermosetting polymer into one or more circumferential frames each shaped to capture the edge of the electrosurgical electrode, an under cut on the circumferential frame for substantially holding and enclosing the edge of the electrosurgical electrode, and a membrane integral with the one or more circumferential frames, the membrane extending from each circumferential frame and coextensive with each circumferential frame, the membrane having a thinness sufficient to allow expansion in deference to the one or more circumferential frames, wherein the one or more circumferential frames, the under cut and the membrane are made from the thermosetting polymer; and wherein the mold cavity is shaped to form the one or more circumferential frames, the under cut of the one or more circumferential frames, and the membrane integral with the one or more circumferential frames.

2. The method of claim 1 with the steps of folding the flexible support and sealing the abutting sides thereof to form a balloon.

3. The method of claim 1 with the steps of inserting a core into the mold cavity to form a balloon during the step of filling.

4. A method of making a support for one or more electrodes comprising:

providing a mold cavity shaped to form one or more circumferential frames, a undercut beneath the one or more circumferential frames, and a membrane integral with the one or more circumferential frames, filling said mold cavity with a polymer, wherein said mold cavity shapes said polymer, and heating said polymer to a temperature to cure said polymer into the membrane with one or more circumferential frames each shaped to capture an edge of each of said electrodes on said support.

5. The method of claim 4 further comprising before filling a mold cavity the act of providing a mold cavity having an unpolished surface finish.

6. A method of molding an electrode balloon comprising:

providing a mold cavity shaped to form a membrane having one or more circumferential frames with an undercut on the frame, filling the mold cavity with a polymer, wherein said mold cavity shapes said polymer;

heating said polymer to a temperature to cure said polymer into the membrane having one or more circumferential frames each shaped to capture an edge of an electrode; and forming said membrane and circumferential frames into a balloon wall.

7. The method of claim 6 comprising after heating said polymer the acts of:

folding said membrane having one or more circumferential frames; and sealing abutting sides of said membrane.

8. The method of claim 6 further comprising before filling a mold cavity the act of providing a mold cavity having an unpolished surface finish to enhance release properties.

* * * * *